(12) United States Patent
Begelman et al.

(10) Patent No.: US 12,073,938 B2
(45) Date of Patent: Aug. 27, 2024

(54) TASK ALLOCATION FOR USE IN MEDICAL IMAGING AND DIAGNOSTICS

(71) Applicant: Canon Medical Systems Corporation, Tochigi (JP)

(72) Inventors: James Lawrence Begelman, Evanston, IL (US); Joseph Manak, Albany, NY (US); Victor Gorin, Buffalo Grove, IL (US); John Baumgart, Hoffman Estates, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 419 days.

(21) Appl. No.: 17/483,267

(22) Filed: Sep. 23, 2021

(65) Prior Publication Data

US 2023/0092780 A1    Mar. 23, 2023

(51) Int. Cl.
*G16H 30/20*   (2018.01)
*G06F 16/901*  (2019.01)
*G16H 40/20*   (2018.01)

(52) U.S. Cl.
CPC ......... *G16H 30/20* (2018.01); *G06F 16/9024* (2019.01); *G16H 40/20* (2018.01); *G06T 2207/10081* (2013.01); *G06T 2207/10088* (2013.01); *G06T 2207/10104* (2013.01)

(58) Field of Classification Search
None
See application file for complete search history.

(56) References Cited

U.S. PATENT DOCUMENTS

| | | |
|---|---|---|
| 8,478,953 B2 | 7/2013 | Pugh et al. |
| 9,576,072 B2 | 2/2017 | Gu et al. |
| 10,650,481 B2 | 5/2020 | Nagao et al. |
| 2020/0042359 A1* | 2/2020 | Zhang .................. G06F 9/5055 |
| 2020/0074584 A1 | 3/2020 | Nagao et al. |
| 2020/0135330 A1 | 4/2020 | Sugie et al. |

\* cited by examiner

*Primary Examiner* — Leon Flores
(74) *Attorney, Agent, or Firm* — Canon U.S.A., Inc. IP Division

(57) ABSTRACT

A control method for controlling data processing acquired from medical imaging modalities by using multiple data processors connected to multiple medical imaging modalities via a network. The method includes obtaining image information for imaging to be performed with an imaging modality from the multiple imaging modalities. The method also includes obtaining load information of the multiple data processors before the imaging is completed. Allocating, based on graph information generated based on the obtained load information, at least a part of the multiple data processors to processing of data acquired in imaging based on the imaging information. The control method may conclude by performing processing of the acquired data with the allocated data processing resource.

19 Claims, 17 Drawing Sheets

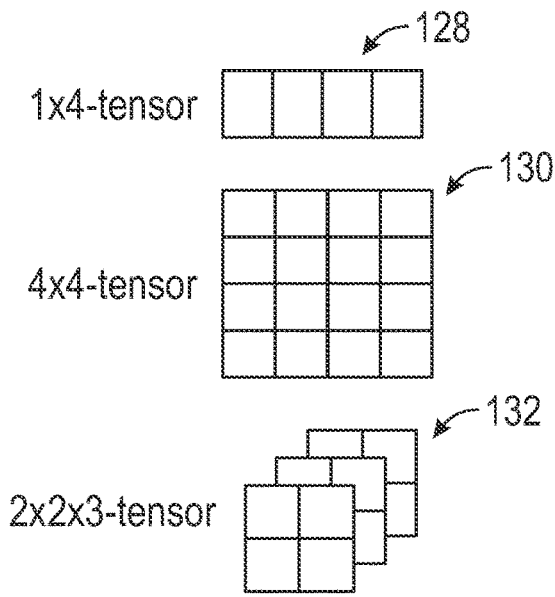
FIG. 5A
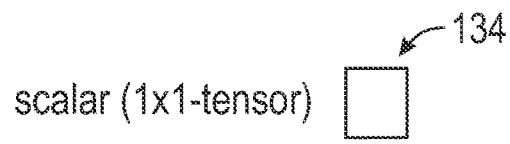
FIG. 5B
|  | name | id | pri | cpu |
|---|---|---|---|---|
| row[0] | "hello" | 123 | 6 | 0.05 |
| row[1] | "world" | 786 | 0 | 0.00 |
| row[2] | "prog" | 11003 | 0 | 25.3 |
FIG. 5C
|  | height | width | type | view |
|---|---|---|---|---|
| row[0] | 128 | 128 | "int" | 6 |
FIG. 5D

TASK ALLOCATION FOR USE IN MEDICAL IMAGING AND DIAGNOSTICS

FIELD OF THE DISCLOSURE

The present disclosure relates generally to the field of medical image processing and diagnostic imaging and more particularly to use of multiple data processors to allocate or distribute image processing tasks in near or real-time for medical imaging and diagnostics.

BACKGROUND

Past imaging system designs have used expensive, dedicated, computing resources to provide high performance image processing. High performance image processing refers to providing image enhancements in real-time as needed for an interventional procedure, near real-time as needed for scan quality control or as quick as possible to minimize clinical procedure times for rapid diagnosis. Dedicating expensive hardware may result in low utilization of a particular imaging system. The hardware is used only when the instrument (imaging modality) to which it has been attached executes a clinical procedure.

Past imaging system software designs have hardwired the dedicated computing resource assumption into their implementations to guarantee performance. This may complicate or prevent evolving designs within and across product lines.

Typical computing resources required to implement real-time or near real-time imaging consists of one or more GPU's housed in a server dedicated for use by a single instrument. The cost of this equipment is high and only in use when the instrument requires imaging to occur. Often this is a small fraction of its duty cycle. Furthermore, within the imaging instrument, computing resources are dedicated for use by a single software application (e.g. CT/MR-reconstruction) to guarantee required performance. As a result, the expensive computing resources have poor utilization. The single software application is also typically designed to use specific models and configurations of GPU's. When the GPU models or their connection topology changes, it may be difficult to port the software to different systems. This may slow introduction of features on different instrument models.

There is a need in the art for a compute processing service to prioritize computations, configured for parallel computations and without requiring software designs hardwired to the computing resource. There is also a need in the art for multiple imaging instruments to share computing resources for increased performance without software modification by adding computing resources to a network shared by the multiple imaging instruments.

SUMMARY

A compute processing service is proposed that discovers and uses available computing hardware transparently with respect to client software, hides computing component models and interconnections from client software so that client software may be moved to different systems, allows multiple medical imaging instruments to share the same computing resources transparently with respect to client software on each system, prioritizes and parallelizes computation across discovered resources transparently with respect to client software, allows computations to be paused and resumed without having to be restarted from their beginnings, reduces client algorithm implementations to CPU/GPU kernel development and facilitates sharing of specific algorithm libraries.

One of the objectives of the present disclosure includes a control method for controlling data processing acquired from medical imaging modalities by using multiple data processors connected to the multiple medical imaging modalities via a computer network. The method includes obtaining imaging information for imaging to be performed with an imaging modality of the multiple medical imaging modalities. The method includes obtaining, before the imaging is completed, load information of the multiple data processors. Allocating, based on graph information generated based on the obtained load information, at least a part of the multiple data processors to processing of data acquired in imaging based on the imaging information. The method then performs processing of the acquired data with the allocated data processing resource.

One or more embodiments of the present disclosure may be used in clinical application(s), such as, but not limited to, medical imaging and research.

According to other aspects of the present disclosure, one or more additional devices, one or more systems, one or more methods and one or more storage mediums using a control method for controlling data processing acquired from medical imaging modalities, by using multiple data processors connected to the multiple medical imaging modalities via a computer network are discussed herein to provide image processing task allocation for near and real-time use. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 5A shows an example of a tensor data type implemented by a compute processing service at a vertex or node of a dataflow graph in accordance with one or more aspects of the present disclosure.

FIG. 5B shows an example of a scalar data type implemented by a compute processing service at a vertex or node of a dataflow graph in accordance with one or more aspects of the present disclosure.

FIG. 5C shows an example of a table data type implemented by a compute processing service at a vertex or node of a dataflow graph in accordance with one or more aspects of the present disclosure.

FIG. 5D shows an example of a parameter list data type implemented by a compute processing service at a vertex or node of a dataflow graph in accordance with one or more aspects of the present disclosure.

DETAILED DESCRIPTION

The present disclosure is directed to a compute processing service for enabling task allocation for real-time and near real-time use in medical imaging and diagnostics. The task allocation or task distribution is accomplished using data processors across a network by distributing computations across one or more compute nodes. An information processing apparatus also known as a compute processing service is deployed on at least one host or a plurality of hosts, where each host includes a data processor or multiple data processors. The compute processing service enables a dataflow service that includes a standard set of compute primitives. The compute processing service enables distributed image processing across a network of medical imaging systems using a plurality of data processors such as CPU's and GPU's.

The compute processing service enables task allocation among different imaging modalities and sharing between multiple active imaging systems. The different medical imaging modalities that may be used with the compute processing service include X-ray, computed tomography (CT) scan, magnetic resonance imaging (MRI), ultrasound and PET scan by way of example. In the present disclosure, X-ray and CT scan imaging modalities are used to describe a control method for controlling data processing acquired from medical imaging modalities using the compute processing service. However, other imaging modalities may be used in addition to X-ray and CT scan or in place of the X-ray and CT scan imaging modalities.

The compute processing service of the present disclosure is applicable in many clinical use-cases including any image reconstruction or related processing. Any computation for volume reconstruction, feature extraction, etc. during real-time or time-sensitive, onsite diagnostic activities. In real-time imaging, the present disclosure applies to any computation that generates graphics/imaging in real time for use during diagnostic or interventional procedures. For real-time or non-real time applications, the present disclosure may apply to any computation (e.g. feedback, registration, etc.) that guides a diagnostic or interventional procedure. The compute processing service allows for wide applications by using the same software to support low-end to high-end imaging systems without modification. The compute processing service accommodates larger caseloads simply by adding computing resources (CPUs, GPUs, FPGA, specialized AI accelerators, etc.) without requiring changes to application software. The compute processing service of the present disclosure minimizes system costs by enabling shared hardware and software computing resources.

Figure 1:
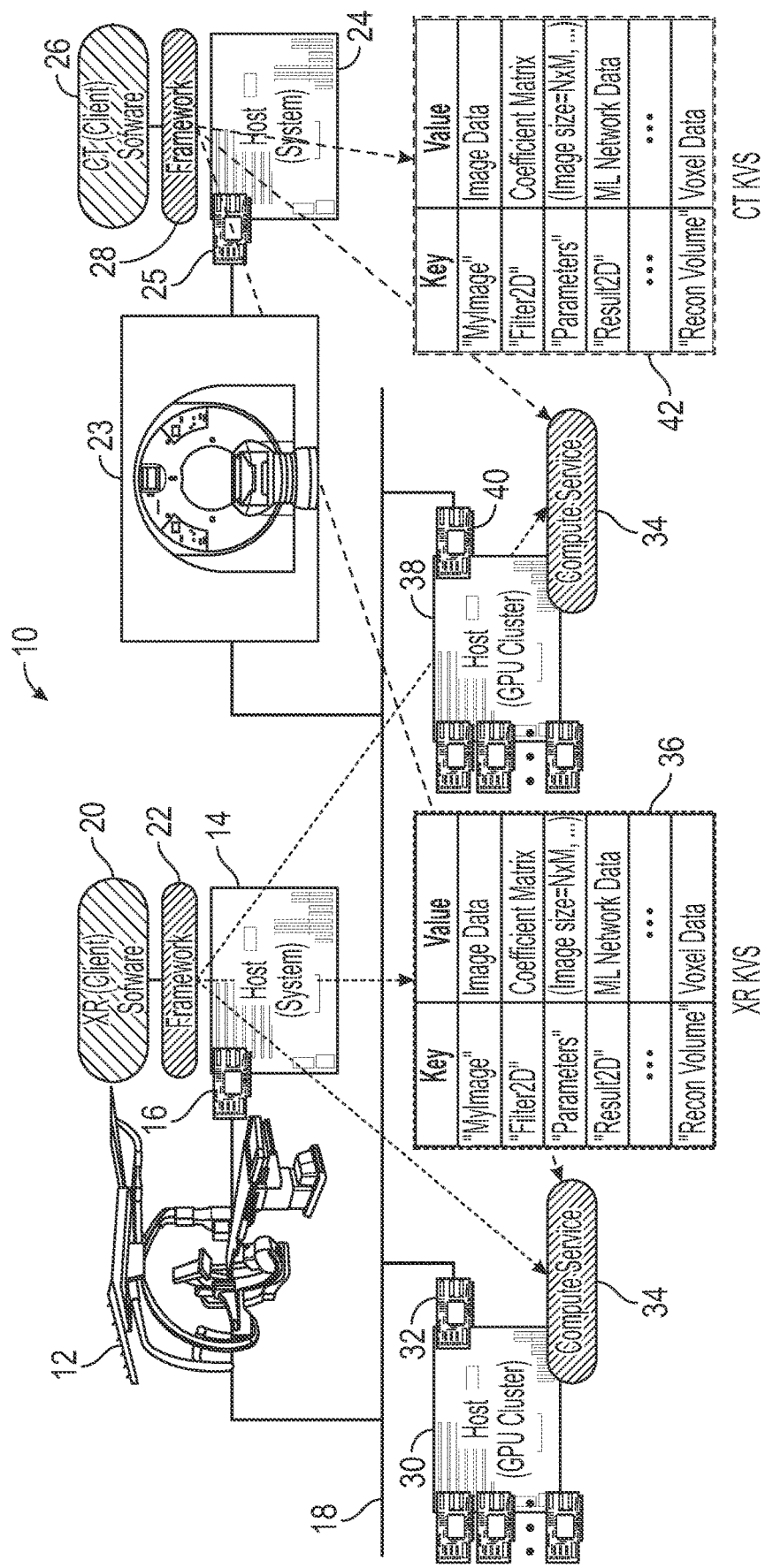
FIG. 1 is a schematic diagram illustrating an overview of imaging systems using a compute processing service to distribute computations across multiple processing units in accordance with one or more aspects of the present disclosure.

Referring now to FIG. 1, a schematic diagram illustrating an exemplary radiology suite 10 consisting of two types of medical imaging systems or modalities by way of example with shared resources. Many radiology suites contain multiple instruments, each of which requires computing resources to perform image processing. Traditionally, the systems have been designed with dedicated resources. The present disclosure facilitates some degree of resource sharing to avoid or minimize the situation where the cost for dedicated resources is too high, the average utilization is low or a combination of the two. Facilitating a degree of sharing lowers the total cost of ownership for the various systems. When shared, both an X-ray system 12 and a computed tomography (CT) system 23 distribute image reconstruction computations across two different hosts (30, 38) in this example. Although two hosts (30, 38) are shown in FIG. 1, the present disclosure may apply to a single host or multiple hosts. The host 30 includes a network interface card (NIC) 32 to communicate via a network 18. The host 38 also includes a NIC 40 to communicate via the network 18. Both hosts (30, 38) include a cluster of graphics processing units (GPUs) to distribute the data processing on the network 18 concurrently. The hosts (30, 38) in this example include a GPU cluster by way of example, the hosts (30, 38) may include a CPU cluster, one CPU or GPU, or a combination of CPUs and GPUs in other examples. The hosts (30, 38) may also include a field-programmable gate array (FPGA) or specialized Artificial Intelligence (AI) accelerators by way of example. Although the radiology suite 10 shows only two imaging systems (X-ray system, CT system), more than two systems may be used in accordance with the present disclosure. Alternatively, the present disclosure also contemplates the scenario where only one imaging system is used.

The X-ray system/imaging modality 12 includes an X-ray host system 14 with a NIC 16 to communicate with data processors distributed across the network 18. The X-ray host system 14 communicates with a client application 20 (third-party X-ray software) and a client service framework 22. The client service framework 22 associated with the X-ray imaging system 12 is used to effectively communicate with a compute processing service 34 using a domain specific language (DSL). The client service framework 22 also communicates with a dedicated key-value store (KVS) 36 via the network 18. The CT system 23 includes a CT host system 24 with a NIC 25 that communicates with a client application 26 (third-party CT software) as well as a client service framework 28 associated with the CT system 23. The CT host system 24 is configured to communicate with the compute processing service 34 of hosts (30, 38) as well as a dedicated KVS 42 associated with the CT system 23 using the NIC 25 to communicate via the network 18. The client service framework 28 associated with the CT system 23 uses the same DSL as the client service framework 22 of the X-ray system 12 to communicate with the compute processing service 34 in a common DSL. The client service frameworks (22, 28) are configured to manage standard data types, key-value store access and dataflow lifecycle and execution.

To share common computing resources, it is required systems execute their processing on the shared resource without interfering in each other's computations. This requires, at a minimum, that the compute processing service 34, keep the data generated by dataflows in the X-ray system 12 separate from the data produced by dataflows in the CT system 23. Additionally, both systems may still need to retain some computing resources as dedicated. The compute processing service 34 uses domains to limit the computing resources and data a dataflow can access during execution. Similar to Linux name space isolation in concept, domains provide resource isolation between groups of dataflows managed by separate systems e.g. the X-ray and CT systems (12, 23) from FIG. 1. Each domain consists of a single, unique key-value store (KVS) and one or more computing resources. Since computing resources can be shared, it is possible for them to be members of multiple domains. A dataflow, however, can be a member of only one domain; and, as a member of that domain, the dataflow can use only the domain's KVS and associated computing resources. A system administrator configures domains. Client applications (20, 26) have no means to manage them programmatically.

Dataflow computations operate on data items stored in the KVS (36, 42), implemented to be global, distributed, and shared among compute processing services on the network 18. Keys are strings and values can be from a small set of standard data types (e.g. scalar, vector, image, volume, table, etc.). The client service frameworks (22, 28) access the KVS (36, 42) by key. Synchronization for concurrent access is not visible to clients (20, 26). The KVS is visible to software clients on all systems. The KVS behaves identically regardless of client location. The KVS is physically distributed, the KVS values may migrate to where needed by executing computations. The lifecycle of stored data in the KVS is independent of client software. Multiple KVS's can be present. Each imaging system is associated with one KVS. To support multi-tenancy, a dataflow computation belonging to a specific imaging system can access only the imaging system's associated KVS.

The compute processing service 34 is a software service that executes processing specifications on a cluster of commodity hardware. Client applications (20, 26) specify the processing to be performed as dataflow graphs. This representation is chosen to express cluster-independent, coarse grained parallelism found in many image processing tasks. Each node or vertex of a graph specifies a processing step. Each edge connecting two vertices specifies the route a result follows from one processing step to the next. The compute processing service 34 is the software component responsible for executing computations specified as dataflow graphs. Execution occurs on a distributed cluster of computing resources, CPUs, GPUs, FPGA, specialized AI accelerators, etc. In the example shown in FIG. 1, the compute processing service 34 is located on hosts with either a CPU or GPU cluster. However, the compute processing service 34 may also exist on the host system of an imaging modality such as the X-ray host system 14 and/or the CT host system 24. The radiology suite 10 shown in FIG. 1 is merely by way of example and various different configurations are contemplated by the present disclosure.

The client applications (20, 26) assign priorities to dataflow graphs dynamically using the client service frameworks (22, 28). Compute processing service instances queue enabled dataflow vertices for execution at the same priority as the dataflow. When dispatched to GPU or CPU, vertices execute in the GPU/CPU run-time environments at the same relative priorities. Dataflow specifications define the type of vertex implementation to use. The compute processing service 34 dispatches vertices according to their implementations (e.g. launch a GPU kernel, activate a CPU thread, message to an application, etc.). Dispatch targets can be any computing resource, local or remote. A thread can be activated on a remote host.

Dispatch selects a computing resource for vertex execution using load balancing policies. Initiation and completion of computations update load metrics to all compute processing service instances. Load balance treats resource selection as network routing. Dispatching computation is analogous to routing a packet to a destination. Computing resources visible from a given dispatcher are considered remote hosts that form a logical overlay network with a mesh topology. Each route has an associated cost equal to the current load on the remote computing resource. Dispatch sends a computation to the resource having the lowest cost route. The routing protocol updates route costs whenever routes change such as when computations start or finish.

The shared compute processing service 34 enables multi-tenant and multi-version operation. Different systems can use the same computing resource concurrently. Different versions of the same processing server software may use the same computing resource concurrently. Each dataflow can specify the version of a vertex implementation it prefers to use. Thus, multiple versions of the same algorithm may be used for backward compatibility.

Dataflows are programs that the compute processing service 34 uses to execute image processing and similar computations. Once generated, dataflows are managed like an application from a client's perspective in that their execution can be started, stopped, paused or resumed. Dataflows represent processing as directed graphs. The graph is a composition of primitive operations whose inputs and outputs are connected together. The primitive operations are represented as vertices of the graph, and the connections between primitives are represented as edges. Graph edges connect the output of one primitive to the input of another. They are directed in that output data generated flows only to the input of other primitives and not in the other direction.

Figure 2A:
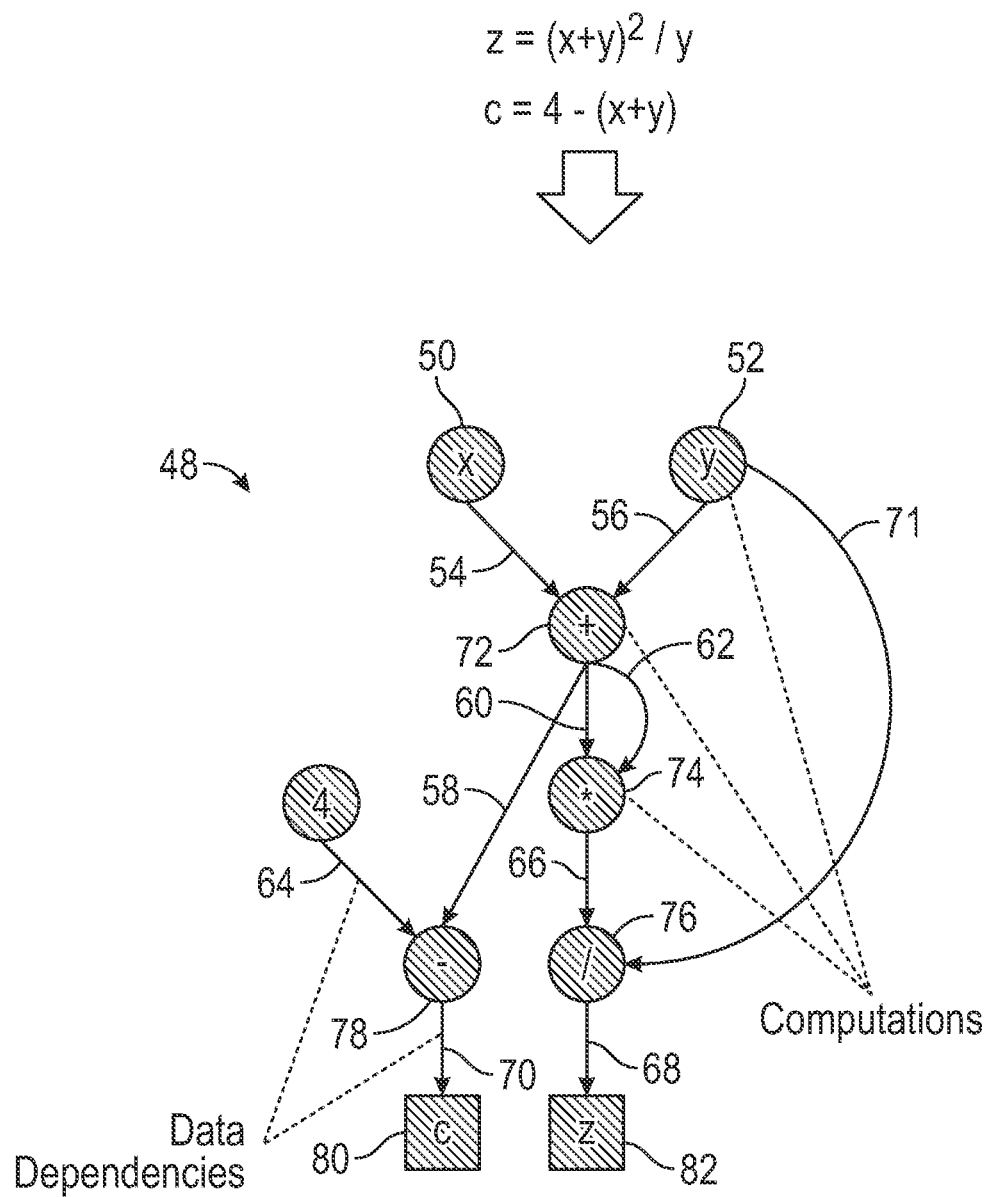
FIG. 2A is a diagram showing an algebraic computation and its representation as a dataflow graph where each node or vertex is a computation that may be distributed across multiple processing units by a compute processing service in accordance with one or more aspects of the present disclosure.

FIG. 2A depicts a simple example of a dataflow graph 48 where the dataflow computes an algebraic formula. The formula is the composite computation built up from primitive arithmetic operations (72, 74, 76, 78). The output of each operation is directed to the inputs of subsequent operations as specified by edges (54, 56, 58, 60 62, 64, 66, 68, 70, 71). The topology of the edges is designed so that the required sub-expressions of the formula are computed, reused, etc. In practice, the primitive computations used for the image processing domain are much more complicated and coarser grained. Typical examples would be algorithms such as Fast Fourier Transforms, Projections, Inference, etc. Similarly, the data flowing through edges would include more complex types than the simple scalar types shown in the example. The dataflow graph 48 in this example includes input X 50 and input Y52 whose values are obtained from a client application. The results of the dataflow graph 48 are represented by c80 and z82 which can then be stored in a KVS.

Figure 2B:
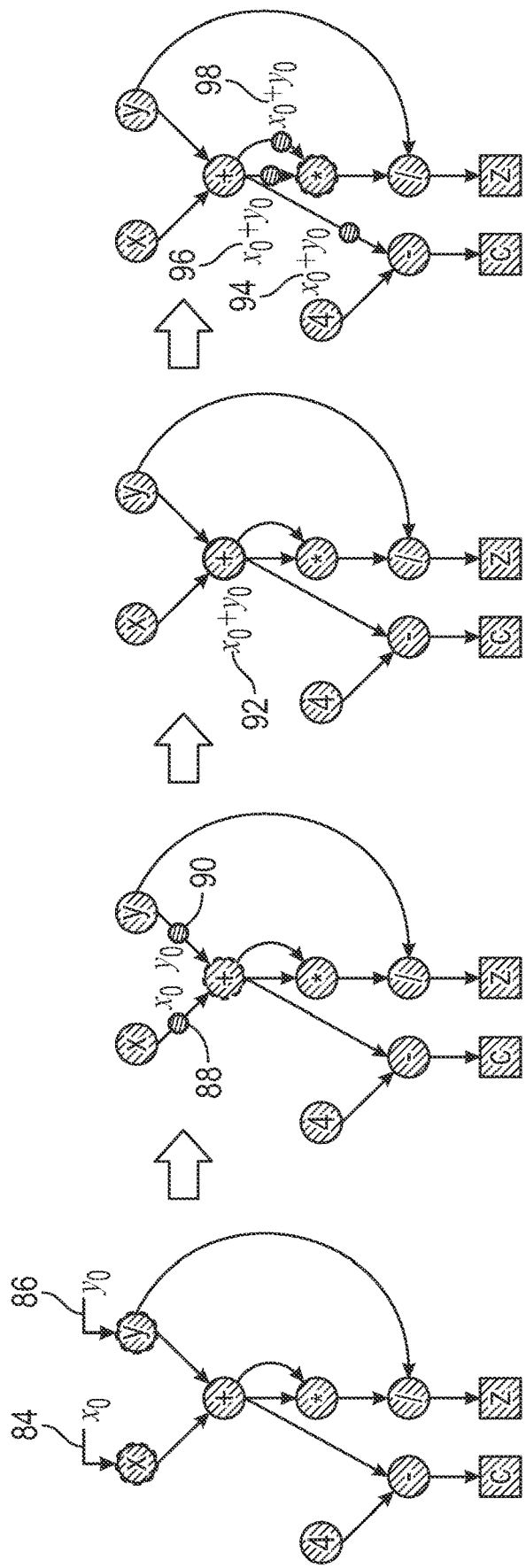
FIG. 2B is a diagram showing the dataflow machine computation model of the dataflow graph in accordance with one or more aspects of the present disclosure.

Dataflow graphs execute using the dataflow model of computation. This model executes graphs by executing all vertices in parallel whose edges have data that is available as the result of prior vertices completing execution. FIG. 2B represents the dataflow machine computation model. Initial values $x_0$ 84 and $y_0$ 86 are supplied from an external source such as a client application from an imaging modality. Computations execute if data is present on all input arcs shown as tokens (88, 90) flowing along the edges. Computations consume data on input arcs when executed 92. Computations place copies of their result onto all output arcs (94, 96, 98).

Figure 3A:
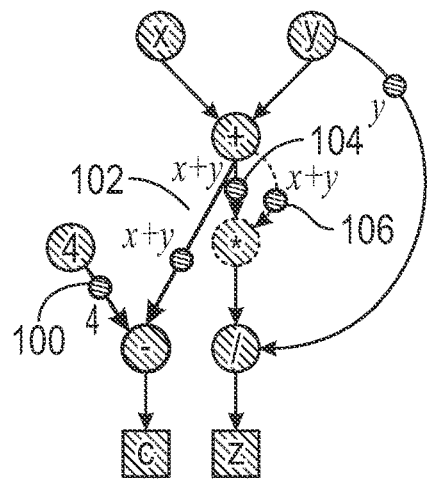
FIG. 3A is a dataflow graph illustrating a parallel data processing approach for a dataflow in accordance with one or more aspects of the present disclosure.
Figure 3B:
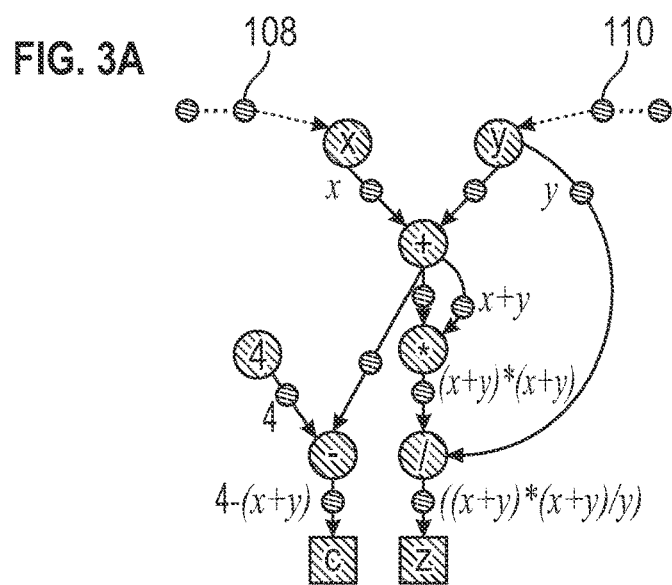
FIG. 3B is a dataflow graph illustrating a pipelined data processing approach for a dataflow in accordance with one or more aspects of the present disclosure.
Figure 3C:
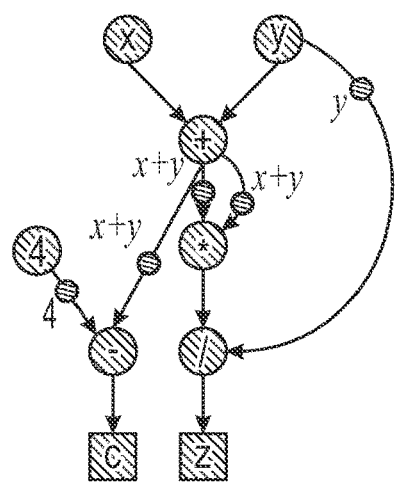
FIG. 3C is a dataflow graph illustrating a data processing approach for eliminating the need to synchronize vertex computations for a dataflow in accordance with one or more aspects of the present disclosure.

The dataflow model of computation is advantageous for the reasons outlined in FIGS. 3A-3C. FIG. 3A shows the dataflow model of computation parallelism advantage. The paths (100, 102) and the paths (104, 106) for example can execute in parallel assuming results from, "x+y", and "4" are present. FIG. 3B shows the pipelined advantage associated with the dataflow model of computation. At any point, each edge can contain data when new values for the input vertices/nodes x and y (108, 110) are supplied continuously. FIG. 3C illustrates the simplicity advantage of the dataflow model of computation. Data flowing on edges is not shared; so, computations at vertices are independent. A need for vertex computations to synchronize is eliminated.

A dataflow can expose the intrinsic parallelism in an algorithm; and, maximize it if the vertex functions are designed appropriately (e.g. specific but generic functions like Fast Fourier Transform). More importantly, the parallelism is expressed in a manner that is independent of the computing cluster configuration within which a dataflow executes. This enables dataflow execution to adapt to computing cluster environments of any size or topology without changes to client software. The dataflow execution model queues data on edges as it is produced by vertex execution. This allows dataflow to pipeline execution when the dataflow graph or portion thereof has a topology consisting of a linear sequence of vertices. Computations with many sequential steps, therefore, can achieve high throughput. Dataflow execution does not share vertex output if that data is sent to multiple destinations. Each downstream vertex can operate on what appears to be its own copy of the output. Downstream vertices, therefore, do not have to synchronize their executions as they operate on separate data. This enables vertices to execute in parallel anywhere in the cluster.

In order to be a highly efficient, flexible and production-ready library, the present disclosure uses dataflow graphs to represent computation in terms of the relationships between individual operations. Dataflow is a programming model widely used in parallel computing and, in a dataflow graph, the nodes/vertices represent units of computation while the edges represent the data consumed or produced by a processing unit. Dataflow are specified with a simple DSL. Clients construct dataflow objects by sending the compute processing service a dataflow specification to compile. The compute service places the compiled form into the current domain's KVS as a dataflow data type. Once a dataflow is placed in the KVS, it is ready for execution.

Representing computation using graphs comes with the advantage of using nodes/vertices to represent operations and edges that represent their dependencies to identify operations that can be executed in parallel. Being a graph, a well-known data structure, it is possible to analyze it with the aim of optimizing execution speed. A graph is a language-neutral and platform-neutral representation of computation. The present disclosure uses a simple language-neutral, platform-neutral, and extensible mechanism for serializing structured data to store graphs. Every graph's node can be placed on an independent device and on a different machine. The compute processing service will take care of the communication between the nodes and ensure that the execution of a graph is correct. Moreover, the compute processing service is able to partition a graph across multiple devices, knowing that certain operations perform better on certain devices.

The present disclosure incorporates image reconstruction capabilities into system designs to be applied in real-time as well as non-real-time contexts. The present disclosure may apply to any computation for volume reconstruction, feature extraction, etc. during real-time or time-sensitive, on-site, diagnostic activities. The computations may create imaging in real-time for use during diagnostic or interventional procedures. The present disclosure is applicable to any computation that guides a diagnostic or interventional procedure.

Figure 4:
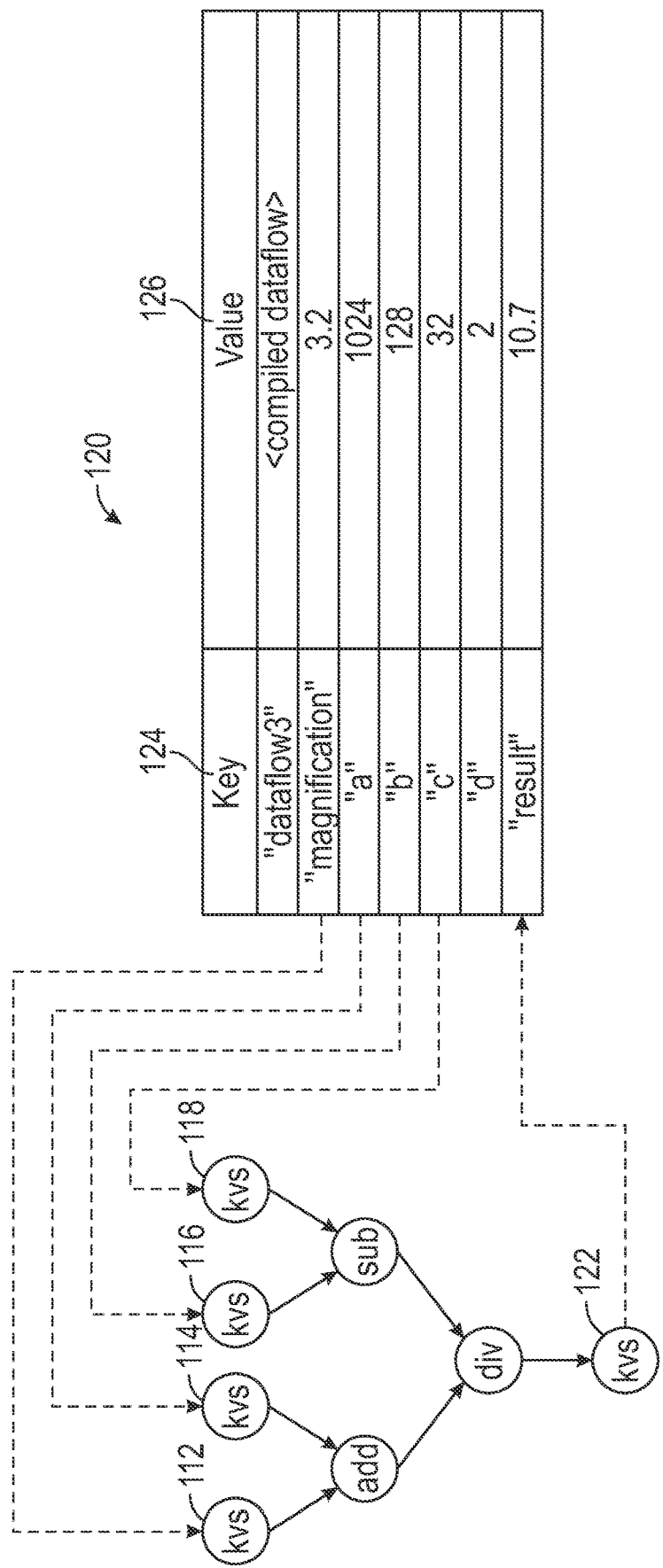
FIG. 4 shows an example dataflow and its use of a key-value store in accordance with one or more aspects of the present disclosure.

The compute processing service key-value store (KVS) stores all data accessed by a dataflow while executing. The KVS contains key-value pairs where each key is a string and the corresponding value can be any one of supported data types: scalar, tensor, table, parameter list or dataflow. One KVS is visible to all dataflows within a domain even if the domain is distributed across the underlying computing cluster. FIG. 4 shows an example dataflow and its uses of the KVS. Four KVS nodes (112, 114, 116, 118) read scalar values from the KVS 120 to provide input for the dataflow. A fifth KVS node 122 writes dataflow results back to the KVS 120. The KVS 120 includes a key 124 which is a string that is part of a key-value pair and the corresponding value 126.

Dataflows read and write KVS items by incorporating input/output vertices into their design. Whenever a KVS item is updated by the client service framework any dataflows using that item for input receive the update. Similarly, whenever a dataflow writes a KVS item any clients blocked reading that dataflow will unblock with the update. The client service framework can repeatedly trigger a dataflow to compute by writing KVS items which the dataflow uses as input; and then, reading KVS items the dataflow produces. The KVS is shared by all dataflows within a domain. This implies that if two dataflows in the same domain use the same key they will reference the same value associated with that key. The KVS is shared by design to allow composition of dataflows. The output of one dataflow can be sent to a specific KVS item; and, a second dataflow can use the same item as its input. More generally, the composition can be one-to-many. If dataflow output updates a KVS item that in turn is used by multiple dataflows for their input then each update of that item can trigger the inputs of the associated dataflows.

Various implementations of image processing software use application specific data types. Images, for example, may have a representation for CT application software that differs from that used by magnetic resonance (MR) application software. These differences in representation are visible in the implementation's source code, making each processing application dependent—typically highly dependent—on its representations of data types. This prevents the processing developed for one application from being easily adapted for use by another. It is ideal if image processing algorithms can be easily reused. To facilitate reuse, the compute processing service supports use of only a small set of general data types. Each vertex in a dataflow can accept only data types from this set; and similarly, it can only output data types that belong to this set. The compute processing service may utilize five different data types, a tensor type, a scalar type, a table type, a parameter list type and a dataflow type.

Referring now to FIGS. 5A-5D, the various data types used by the compute processing service are illustrated. A tensor is similar to a TensorFlow tensor. It is a multidimensional array of a finite number of dimensions. Each dimension has a size, the number of elements along that dimension, giving the tensor a "shape". In FIG. 5A, the tensor examples show a one-dimensional tensor 128, two-dimensional tensor 130 and three-dimensional tensor 132 where each has a unique shape. Tensor elements contain either reals or integers, but all the elements of a given tensor must be the same type.

FIG. 5B illustrates an example of a scalar type 134. The scalar type 134 includes a scalar that is a one dimensional tensor of one element that can contain either a single real number or a single integer. Because scalars are used frequently, the compute processing service provides this specialization of a tensor for convenience. FIG. 5C illustrates a table type 136. The table type 136 is a table similar to a relational database table. It is a 2-dimensional array of elements where each column has a name and each row has a unique numeric identifier. Unlike tensors, table elements can be one of the following data types: strings, scalars, or tensors. Tables can be searched in a variety of ways. They can be scanned by row, by column or individual elements can be indexed directly. FIG. 5D illustrates a parameter list type. The parameter list type includes a parameter list 138 which is a table having only one row. Parameter lists, like scalars, are used frequently, so the compute processing service provides this specialized form of a table as a convenience. Because parameter lists have only one row, a row index is never required to locate an element or scan the list.

List elements can be indexed only by their column names, making parameter lists equivalent to a list of key-value pairs or a map.

Compiled dataflows are another data type, once compiled a dataflow is placed into the compute processing service KVS using the dataflow name as the KVS key and the compiled dataflow as the KVS value. The representation of the dataflow is not visible to a client. The dataflow type is simply a sequence of bytes treated as a single object. The client service framework, however, can read compiled dataflows from the KVS in order to save the compiled representation in a file of the client's choosing. Clients can reopen this file at a later point, read the dataflow into memory, and write it back into the KVS. After the KVS has been updated, the dataflow can be treated like any other compiled dataflow. The dataflow type provides a means to restore dataflows without associated compilation overheads.

Figure 6:
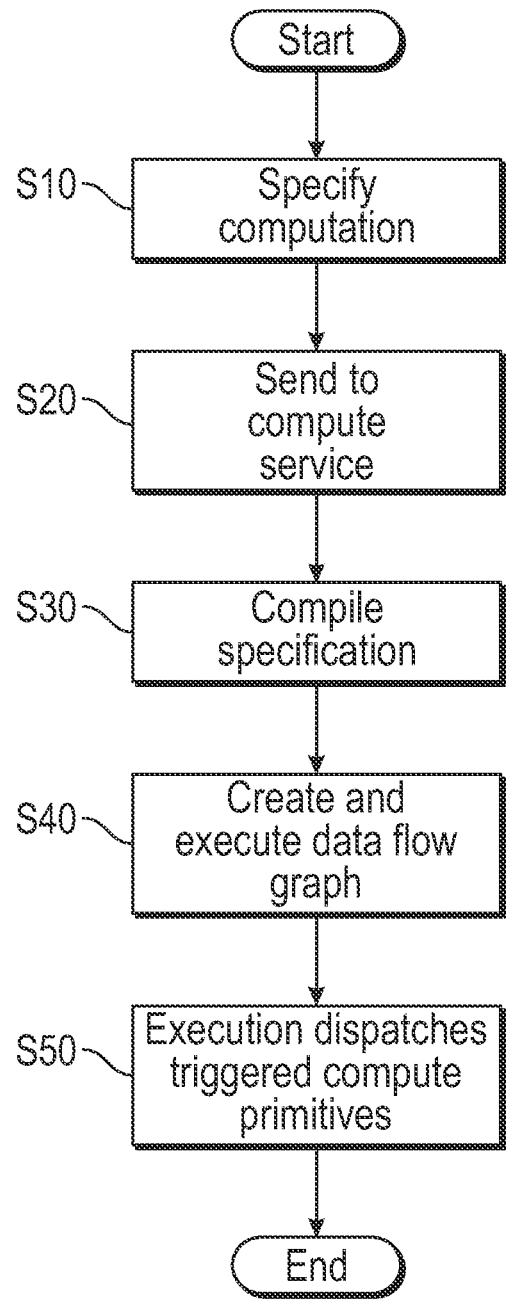
FIG. 6 is a flowchart illustrating the steps for specifying computation as dataflow graphs whose nodes or vertices represent compute primitives in accordance with one or more aspects of the present disclosure.
Figure 7:
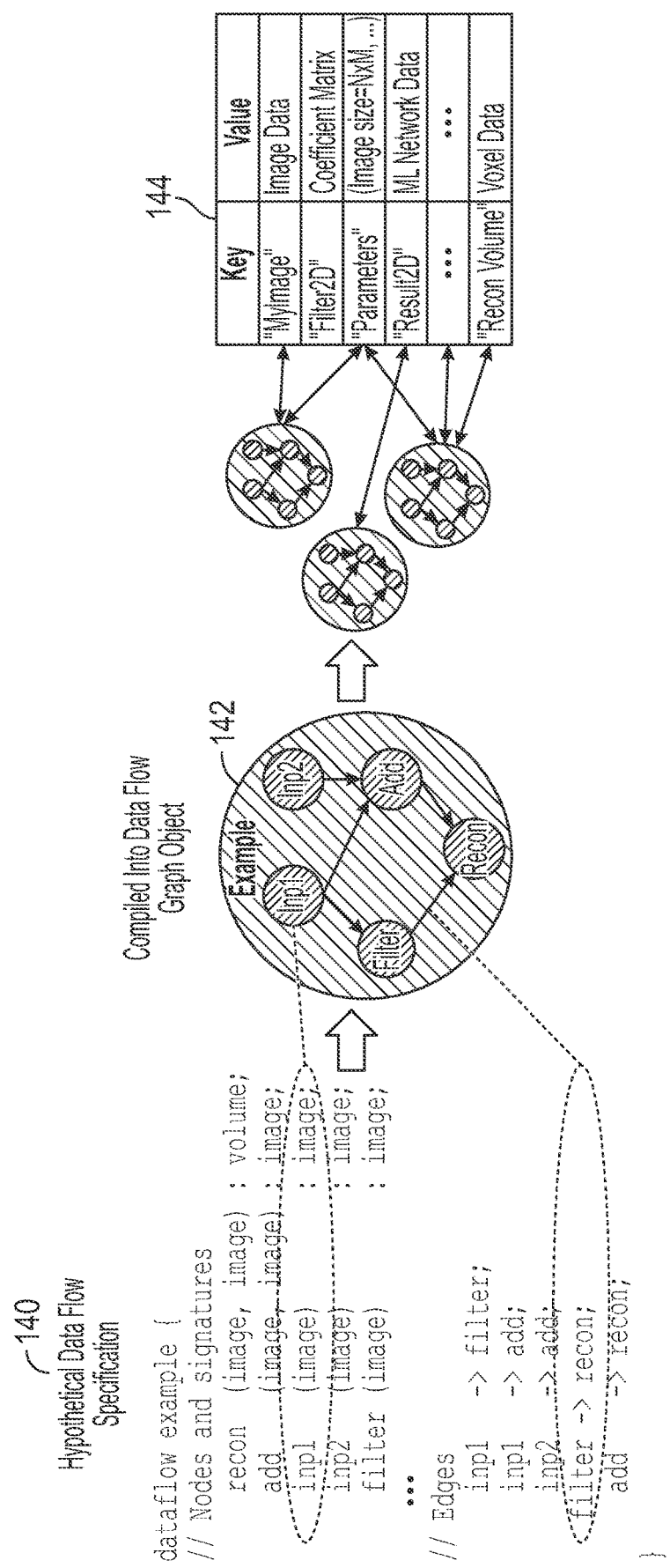
FIG. 7 is a schematic diagram illustrating a hypothetical dataflow specification in a domain specific language is compiled into a dataflow graph that uses a key-value store in accordance with one or more aspects of the present disclosure.

FIG. 6 is a flowchart illustrating the process to setup a dataflow and initiate the dataflow by the client application associated with a medical imaging modality as well a data processor associated with the compute processing service. In step S10, the client service framework specifies computations based on information received from the client application. The information received from the client application includes imaging information that is obtained from the imaging modality associated with the client application such as an X-ray system or CT system for example. The computations may include image reconstruction or image processing computations. However, the computations are not limited to image processing and image reconstruction. The computations could include artificial intelligence inference, statistics, etc. Then the client application sends the computations to the compute processing service 34 in step S20 in the form of a dataflow graph. The compute processing service 34 compiles a data flow specification in step S30 in order to create and execute the dataflow graph. Upon receiving the dataflow graph, the compute processing service 34 executes the dataflow graph in step S40. If the compute processing service 34 has multiple data processors available across the network, the compute processing service 34 may dispatch nodes of the dataflow graph on any computing resource (local or remote). Dispatching nodes of the dataflow graph select a computing resource for execution using load balancing information. Load balancing information may be obtained by the compute processing service 34 by analyzing a network route. Each route has an associated cost equal to the current load on the remote computing resource. The compute processing service 34 dispatches a computation to the resource having the lowest cost route. The routing protocol updates route costs whenever routes change as a result of computations starting or finishing. FIG. 7 illustrates a hypothetical data flow specification 140 that is then compiled into a dataflow graph object 142 by the compute processing service 34. The dataflow graph objects are then executed using values from a KVS 144. The client service framework uses a domain specific language to specify data flow computations to generate dataflow graph objects.

Referring back to FIG. 6, in step S40, the compute processing service 34 generates and executes the dataflow graph. In step S50, the compute processing service 34 dispatches triggered compute primitives. Compute primitives are preregistered with the compute processing service 34 via an application that is stored on the compute processing service 34. The compute processing service 34 also includes shared libraries and GPU kernel to dispatch triggered compute primitives. In other words, the compute processing service 34 execute triggered vertices of the generated dataflow graph. Complex computations are specified as dataflow graphs whose vertices represent compute primitives. All compute primitives are packaged as shared libraries. Compute primitives can be implemented as GPU-kernels, shared objects or applications. Each compute primitive (vertex/node) in a dataflow graph corresponds to some software that is built and packaged as a software library (shared library) that is deployed with the compute processing service 34. Each library exports a well-known function that the compute processing service 34 knows how to call in order to execute the vertex/node. When the compute processing service 34 is started, it scans the installation area for these libraries and dynamically links their functions into the server. Subsequently, when the client service framework creates a dataflow, the compute processing service 34 compiles the dataflow graph. As the compiler encounters each vertex definition in the domain specific language, it searches its internal vertex database to match vertex with implementation. The shared library is a software library that is developed by researchers or engineers to implement primitive components required for image processing dataflows. A dataflow engine or dataflow service of the compute processing service 34 executes the dataflow graphs by dispatching sets of graph nodes in parallel as their inputs become available. Dataflow graph execution is the process by which compute processing service 34 software makes data flow through the graph.

The graph execution model uses the dataflow model of computation. Each vertex of a dataflow is examined to determine if all of its inputs are present. If so, the vertex is considered to be executable and added to the set of executable vertices. Once all vertices in the dataflow have been checked, the set of executable vertices are dispatched to execute in parallel. If there are enough computing resources to execute each vertex in the set concurrently, then the execution achieves perfect parallelization. If there are few resources then some degree of serialization will occur. In either case, the degree of parallelization is independent of the dataflow. As each vertex completes execution, its output is delivered along all outgoing edges to one or more destinations (i.e. dependent vertices). The outputs become new inputs for the destination vertices. The process is repeated until all vertices in the dataflow are not executable. The dataflow model of computation executes a vertex if and only if all of its inputs are present. In practice there is some amount of time between "inputs being present" and the vertex actually "executing." When inputs are present, a vertex is ready for execution but not yet executing. The vertex is said to be triggered when ready for execution but not yet executing. A triggered vertex then has to be told to start execution. The terminology is to dispatch a vertex.

Figure 8:
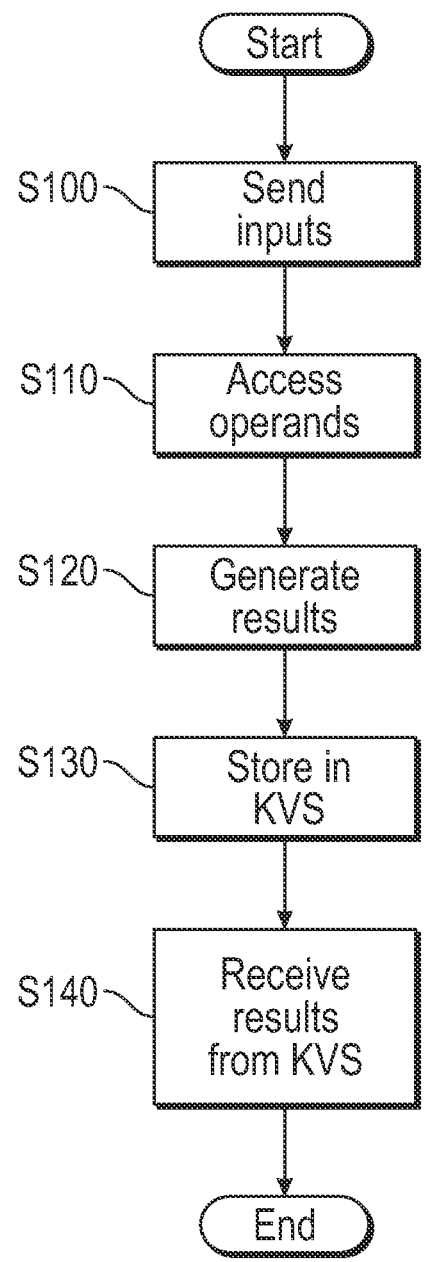
FIG. 8 is a flowchart including various steps a client application and a compute processing service access a key-value store to input and update computations on a node or vertex of a dataflow graph in accordance with one or more aspects of the present disclosure.

Referring now to FIG. 8, the flowchart includes various steps outlining a process for computing the dataflow by the compute processing service 34 in accordance with the present disclosure. The computation may initiate when the client application built with the client service framework, packaged as a library sends inputs to trigger execution of computation in step S100. The inputs are stored as keys in a KVS. Alternatively, a third party may send inputs to trigger execution of computation instead of the client application. The state of a computation, the set of all vertex operands in a dataflow graph, is maintained in a KVS which is a global, distributed, shared, associative memory. In step S110, the compute processing service 34 access operands and create results which are then stored as values in the KVS. The compute processing service 34 creates results using an application, shared library and a GPU kernel. For example, the GPU kernel accesses the value stored in the memory or KVS. Once the value is accessed the GPU kernel of the compute processing service 34 generates a result in step S120 and stores the result back to the KVS in step S130. Then the client application using the client service framework receives the results when available in step S140. The client application receive results when the KVS updates.

Figure 9:
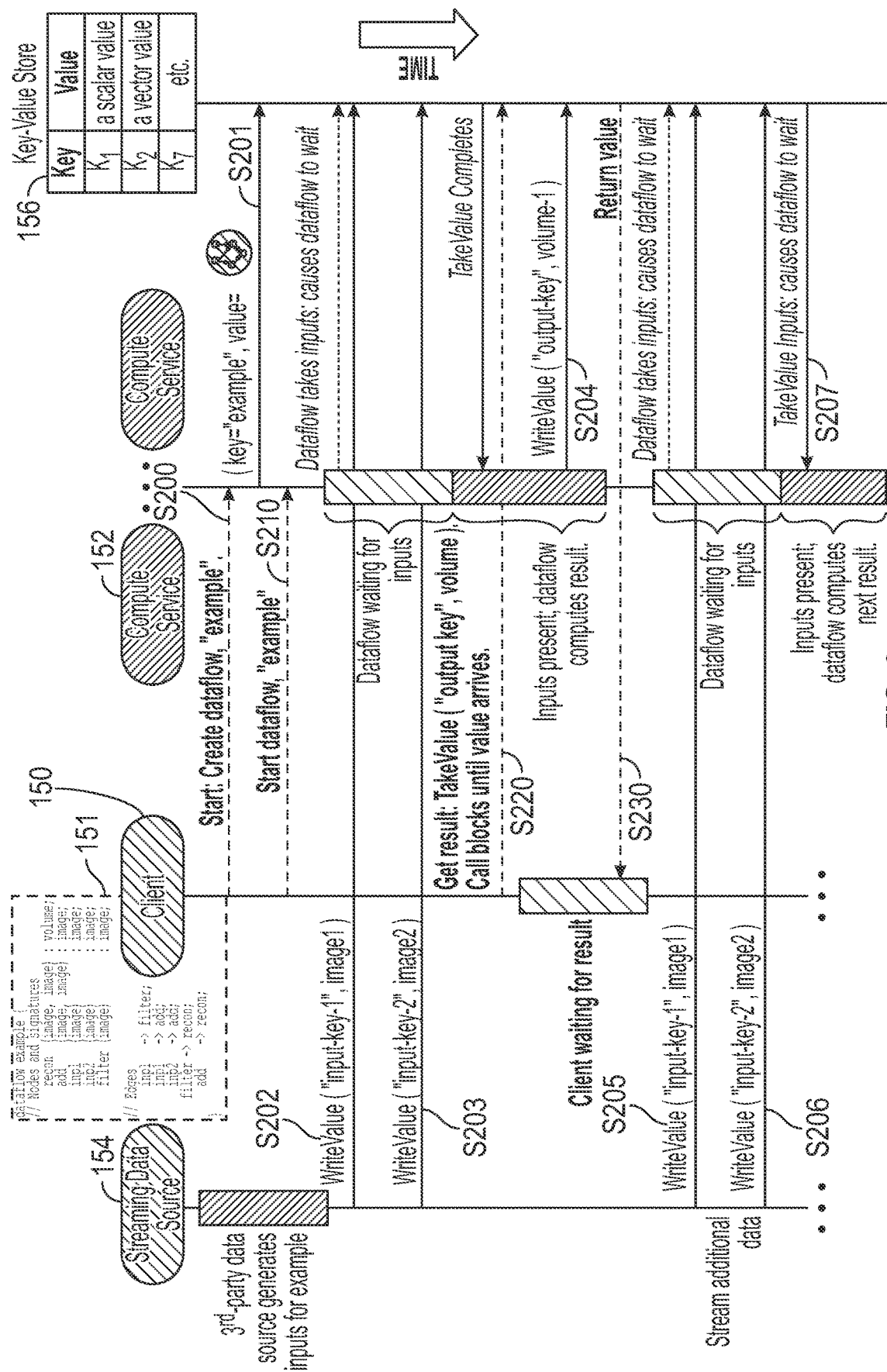
FIG. 9 is a diagram showing various communications between a client application, streaming data source, compute processing service and key-value store in accordance with one or more aspects of the present disclosure.

Referring now to FIG. 9, a schematic diagram illustrating a programming view of the client service framework 150 is shown. The client service framework iso compiles a dataflow specification 151 to create a dataflow labeled "example" in step S200 and transmits the dataflow to a compute processing service 152 or a plurality of compute processing services on the network. In step S201 the compute processing service 152 stores the key "example" and the dataflow graph as the value in the KVS 156. The client service framework iso may then initiate computation of the dataflow "example" in step S210 by transmitting an instruction to the compute processing service 152. In steps S202 and S203 input values are transmitted from a streaming data source 154 to the KVS 156. The streaming data source 154 may be a third party data source that generates inputs for example. Alternatively, the input values may be transmitted to the KVS 156 from an imaging system via the client service framework iso. In step S220 the client service framework 150 requests results from the KVS 156 once the inputs are present and the dataflow computes results, the KVS 156 returns the results to the client service framework 150 in step S230. The compute processing service 152 initially waits for the inputs, then once the inputs are received, the compute processing service 152 updates the KVS 156 with the results which the client service framework 150 is able to receive by accessing the KVS 156. The results may be updated when additional data is transmitted from the streaming data source 154 to the KVS 156 in steps S205 and S206. The compute processing service 152 updates the KVS 156 to compute the next result.

Figure 10:
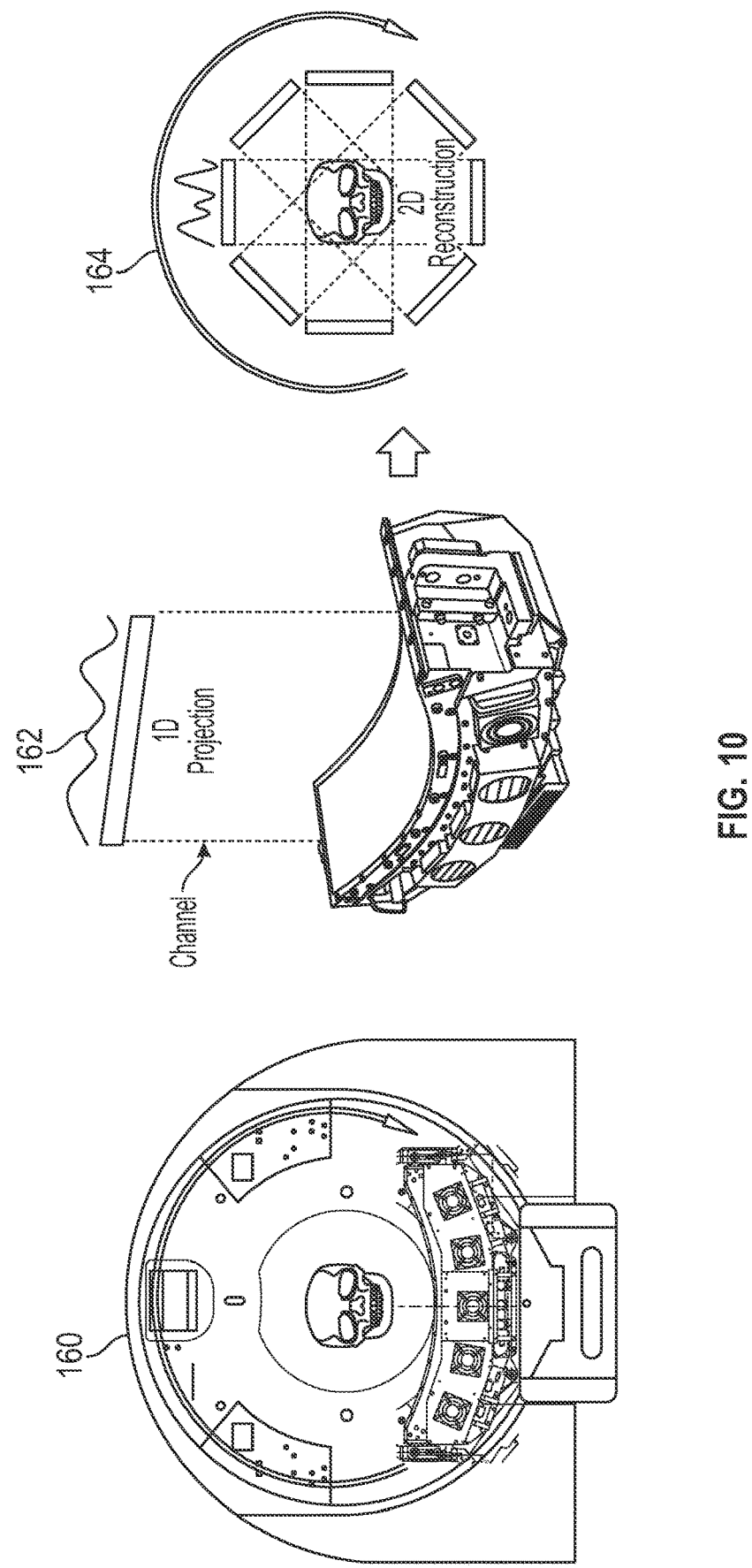
FIG. 10 illustrates a CT scanner system used as a single host for image reconstruction in accordance with one or more aspects of the present disclosure.
Figure 11:
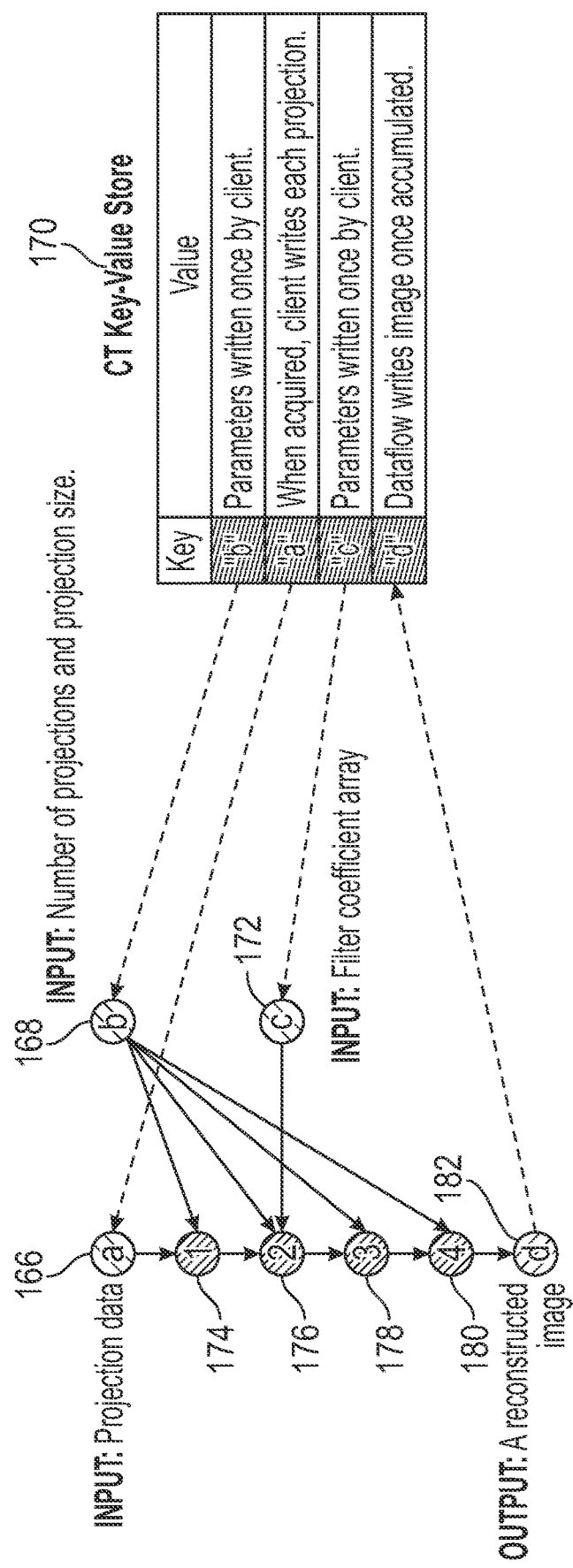
FIG. 11 is an example of a dataflow graph and key-value store for image reconstruction on a single host from FIG. 10 in accordance with one or more aspects of the present disclosure.

Referring now to FIG. 10, a computed tomography (CT) scanner system 160 acquires multiple projections at different orientations. In the following example, the projections are from a single channel 162. It should be noted that in practice, detectors have multiple channels. Reconstruction of a single slice uses multiple one-dimensional projections to form a two-dimensional image 164. FIG. 10 is an example of image reconstruction on a single host (CT imaging system 160) in accordance with the present disclosure. The image reconstruction from the single host involves a dataflow graph as shown in FIG. 11. The dataflow graph is for reconstruction on a single host. A dataflow graph for basic fan-beam reconstruction is shown. In this example, the dataflow graph accepts one projection at a time, but can execute up to four operations in parallel once enough projections have been sent to fill the processing pipeline. Vertex a 166 is a projection such as a one-dimensional tensor type also known as a vector. Vertex b 168 represents the number of projections and projection size (parameter list). Vertex c is a filter coefficient array (one-dimensional tensor type data). The vertices a, b and c (166, 168, 172) represent the inputs of the dataflow graph. Vertex 1 174 represents weight projection. Vertex 2 176 is a filter projection and vertex 3 178 is a back project a projection into an image. The computation defined by vertex 3 produces an image from a single vector, the projection. Vertex 4 180 accumulate images up to a specific limit. The limit is determined by the number of projections defined in vertex b 168. The vertices 1 through 4 (174, 176, 178, 180) represent the operation vertices. The output vertex d 182 is a two-dimensional "tensor type" also known as an image and represents the output or result of the dataflow graph.

The dataflow graph input/output vertices read/write KVS elements. Input vertices read (or take) the corresponding KVS elements as soon as they are written by the client. Output vertices write or update the corresponding KVS elements when data arrives at the output vertex. In FIG. 11, a KVS 170 associated with the CT system 160 is shown. The KVS 170 stores the input and output vertices of the dataflow graph in the key of the KVS 170 as well as the values associated with each key. The dataflow graph input and output vertices read and write KVS 170 elements. Input vertices read (or take) the corresponding KVS 170 elements as soon as they are written by the client service framework. Output vertices write (or update) the corresponding KVS 170 elements when data arrives at the output vertex.

Figure 12:
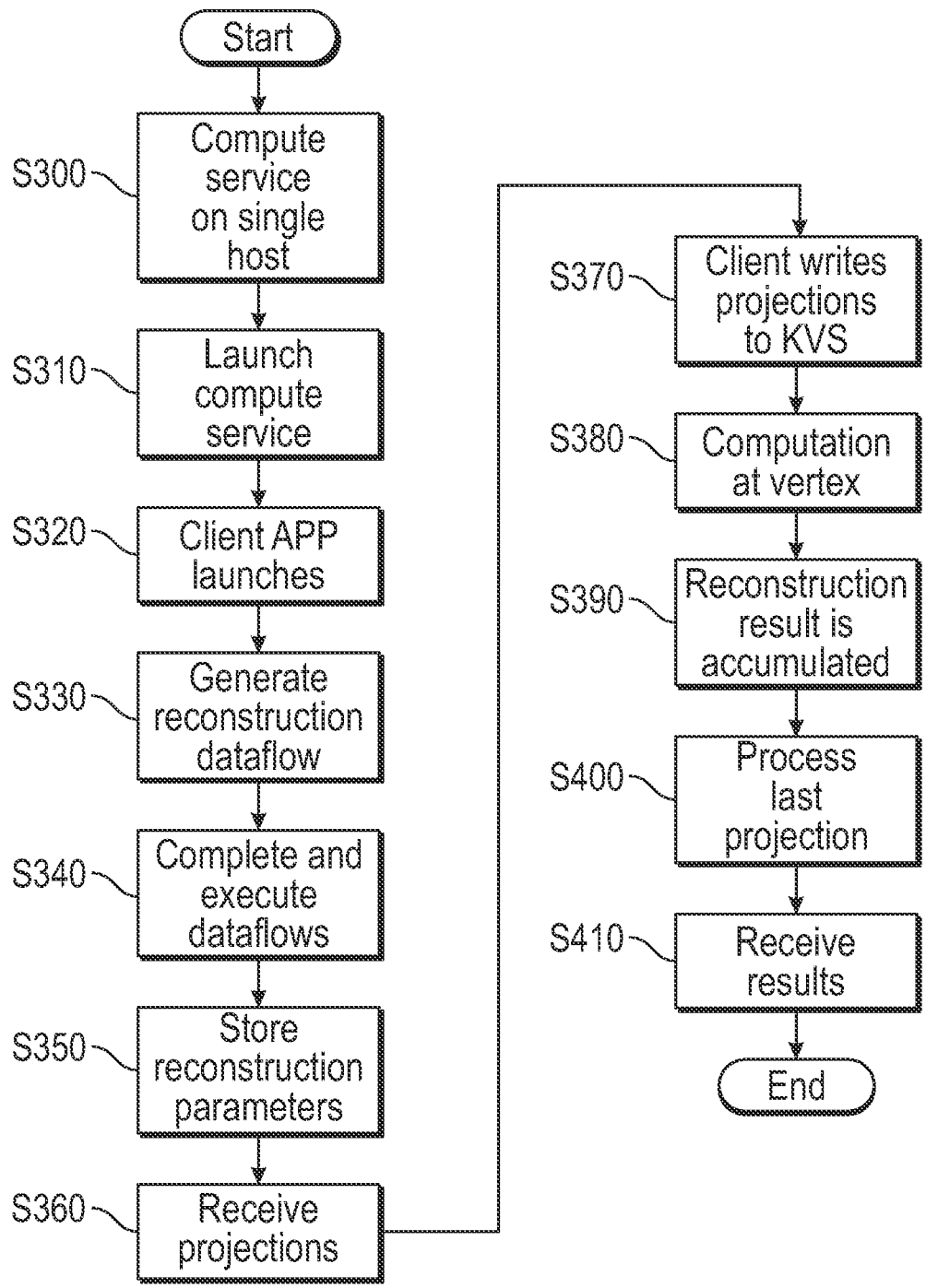
FIG. 12 is a flowchart showing various steps for image reconstruction on a single host in accordance with one or more aspects of the present disclosure.

FIG. 12 is a flowchart illustrating the process for image reconstruction on a single host. In step S300, the client application and the client service framework including all executable compute processing service components are installed on a single host. The components of the compute processing service include the client service framework, shared libraries, built-in algorithms and vertex implementations. The vertex implementations by way of example may include weight, filter, back-project, etc. as shown in FIG. 13. In step S310, the compute processing service is launched during system startup. In this example, the system is a CT imaging modality 160. The compute processing service is configured to discover available computing resources such as GPU or CPU clusters on the network as well as algorithms. In this example, one CPU and one GPU are discovered. In step S320, when the client application launches, the client service framework discovers the compute processing service. In step S330, the image reconstruction dataflow is generated. This occurs when the client service framework creates the reconstruction dataflow by sending a dataflow specification to the compute processing service. The compute processing service in step S340 compiles the dataflow specification and starts executing the dataflow. However, no vertices of the dataflow graph are enabled for execute, so no computations occur. In step S350, the image reconstruction parameters are stored in a KVS. In particular, the client service framework sends the image reconstruction parameters to the KVS. In step S360, projections are received by the client service framework from the CT system 160. An acquisition is initiated that begins to produce projections from the imaging modality (CT system 160) that are sent to the client service framework. In the case of post-procedure, batched or queued, use-case, projections may be produced by reading them from storage.

Next, in step S370, the client service framework writes the projections to the KVS. Alternatively, the CT system 160 may write the projections directly to the KVS. In step S380, the computations at the vertex are initiated. The dataflow input vertex takes each projection from the KVS as it arrives and produces the projection on its output edge. An input/output vertex computation is defined as either taking, reading or writing items in the KVS. In step S390, the image reconstruction result is accumulated. Processing vertices are now enabled so the compute processing service dispatches them to the GPU for execution. The reconstruction result is accumulated as the dataflow produces a sequence of back projected images. Concurrently, the client application is sending the remaining projections. In step S400, the last projection is processed. Once the last projection has been processed, the dataflow accumulation vertex writes the final result to its output edge. The output vertex then writes the result to the KVS. In step S410, the client application receives the results when the results arrive in the KVS.

Figure 13A:
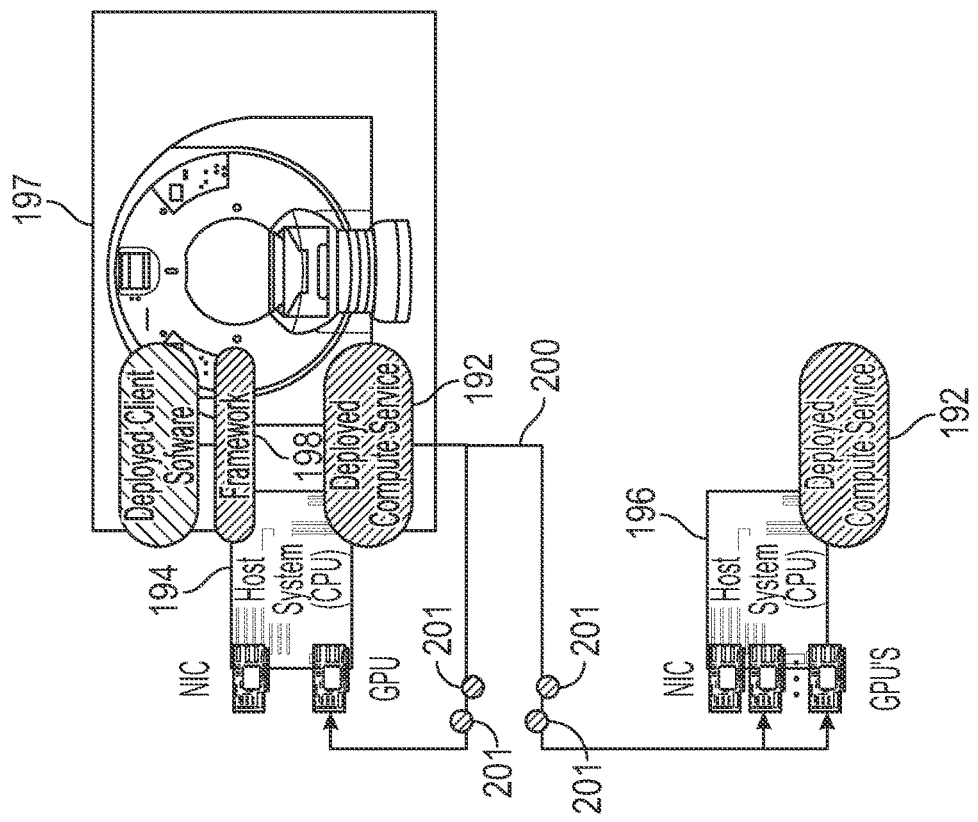
FIGS. 13A and 13B are schematic diagrams illustrating an exemplary image reconstruction on multiple hosts in accordance with one or more aspects of the present disclosure.
Figure 13B:
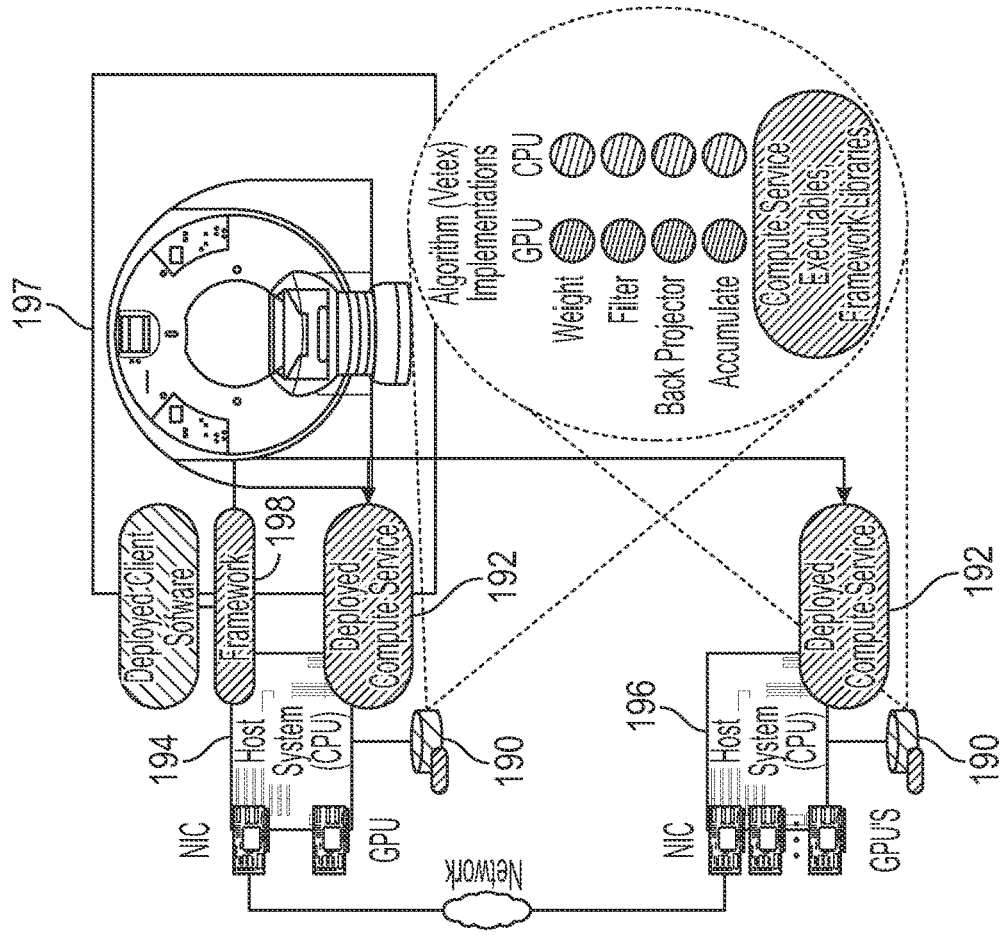

FIG. 13A is a schematic diagram of a multiple host system for image reconstruction in accordance with an aspect of the present disclosure. The software components 190 are installed on multiple host system (194, 196) in a similar manner as the single-host reconstruction use-case. The compute processing service 192 is in communication with the multiple host system (194, 196) and distributed across the network. The components of the compute processing service include the client service framework, shared libraries, built-in algorithms and vertex implementations. The vertex implementations by way of example may include weight, filter, back-project, etc. The compute processing service 192 is configured to launch at the imaging modality 197 system startup. The compute processing service 192 are configured to discover available computing resources and algorithms. In this example, the CPU's and GPU's belonging to the two different hosts (194, 196) are discovered. When the client application associated with the imaging modality 197 launches, the client service framework 198 discovers the compute processing service 192. Image reconstruction proceeds identically as in the single-host use case described above with respect to the flowchart of FIG. 12 with the exception that vertices 201 of the dataflow graph can be dispatched to execute in parallel 200 across multiple compute resources as shown in FIG. 13B.

Figure 14B:
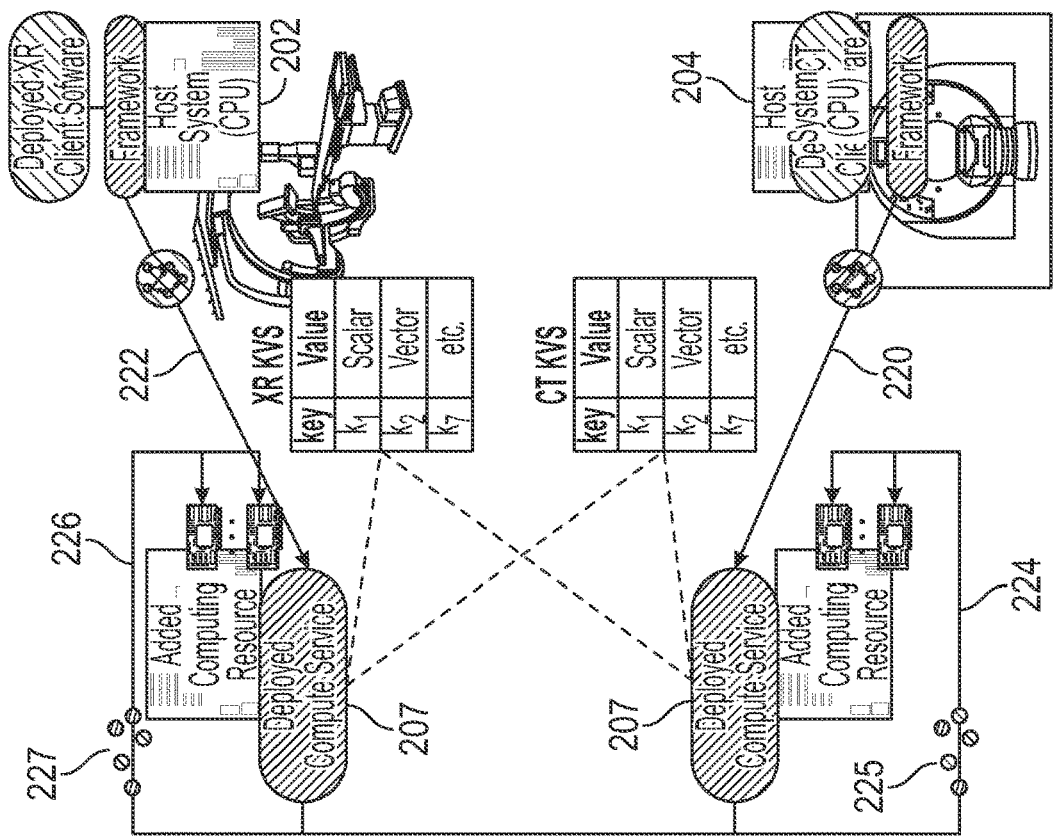
FIGS. 14A and 14B are schematic diagrams illustrating an exemplary image reconstruction on multiple imaging systems and multiple hosts in accordance with one or more aspects of the present disclosure.
Figure 14A:
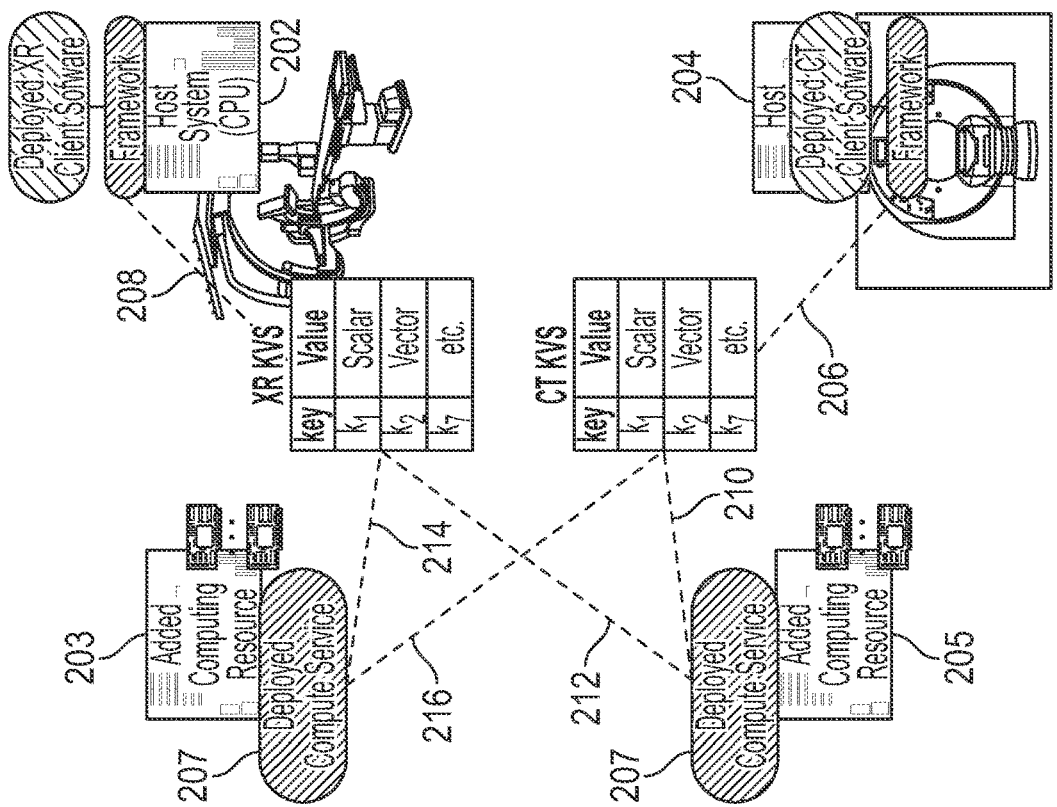

FIG. 14A is a schematic diagram representing image reconstruction on multiple imaging systems and multiple hosts in accordance with an aspect of the present disclosure. It should be noted that the network and network interface cards are not shown in FIG. 14. In this embodiment, software components are deployed to multiple system hosts and compute resources in a similar manner shown in FIG. 13A with respect to the multiple host scenario. The host system 202 is for an X-ray imaging modality including X-ray client software and a client service framework deployed on the host system 202. The host system 204 is for a CT imaging modality including CT client software and a client service framework. The deployed compute processing service 207 are included with the added computing resources (203, 205). The compute processing service 207 is configured to discover the available computing resources in the same manner as in the multiple host scenario of FIG. 13. The client service frameworks discover the compute processing service in the same manner as the multiple host scenario of FIG. 13. The client service frameworks connect only to their pre-configured, system specific, KVS. In this example, the host system 202 for the X-ray imaging modality is in communication 208 with the X-ray KVS. The host system 204 for the CT imaging modality is in communication 206 with the CT KVS. The compute processing service 207 may use multiple KVS's depending on which dataflow vertices get dispatched to their computing resources. In this example the compute processing service 207 associated with the added computing resource 203 may communicate 214 with the X-ray KVS as well as communicate 216 with the CT KVS. Similarly, the added computing resource 205 includes the compute processing service 207 which communicates (210, 212) with the two different KVS (X-ray KVS and CT KVS).

Referring now to FIG. 14B, the host systems (202, 204) create dataflows (220, 222) that the client service framework assigns to any of the compute processing service 207 in the same manner as the multiple-host scenario. Each compute processing service dispatches vertices (225, 227) to all compute resources. A given vertex depending to which dataflow it belongs, uses only a single KVS for its operands and results. The vertices 225 from the CT dataflow use the CT KVS when dispatched and the vertices 227 from the X-ray dataflow use the X-ray KVS when dispatched.

The compute processing service is also configured to perform task allocation based on reservation information that is obtained from a Radiology Information System (RIS) or a Hospital Information System (HIS). In the examples described above the dataflow graphs are compiled by the compute processing service using imaging information obtained from an imaging modality. However, the imaging information may be obtained by a RIS or HIS. Additionally, the compute processing service may set a priority for each computation based on the reservation information. For example, a computation for an urgent examination may take priority over a computation associated with a regular examination. Even in a scenario where the computation for a regular examination begins before the computation for the urgent examination, the compute processing service is configured to pause the computation for the regular examination in order to complete the computation for the urgent examination.

The compute processing service is also configured to perform task allocation based on protocol information from an imaging modality. For example, the compute processing service is able to determine data processors to perform each computation in view of (i) the specification of the type of imaging modality (CT, MRI, X-ray, Ultrasonic, etc.), (ii) a type of imaging reconstruction process to be performed, or (iii) a type of filter process to be performed. One way in which the compute processing service may distinguish between dataflow graphs of varying priority is by the way the dataflow graph is named. A domain specific language (DSL) may be used for naming the dataflow graphs. In this way, the compute processing service is able to prioritize calculations based not only a type of imaging modality or hardware but also the prioritization may be temporally driven or resource driven. Dataflows may be suspended and resumed based on resources available or needed. Thus, a particular DSL associated with the dataflow graph names allow for the compute processing service to determine an order for executing computations associated with various dataflow graphs.

One example of prioritization may include the compute processing service determining that an imaging modality such as an ultrasonic diagnosis device takes precedence over at least one other imaging modality. The compute processing service may determine based on the dataflow graph name that the computations are for an ultrasonic diagnosis device and determined that the computations take precedence over computations associated with a CT imaging device. A user or operator of the compute processing service may designate an imaging modality to be prioritized such that the compute processing service allocates resources in view of the user designated priority. For example, computations associated with the designated modality will complete prior to computations associated with a different imaging modality.

Figure 15:
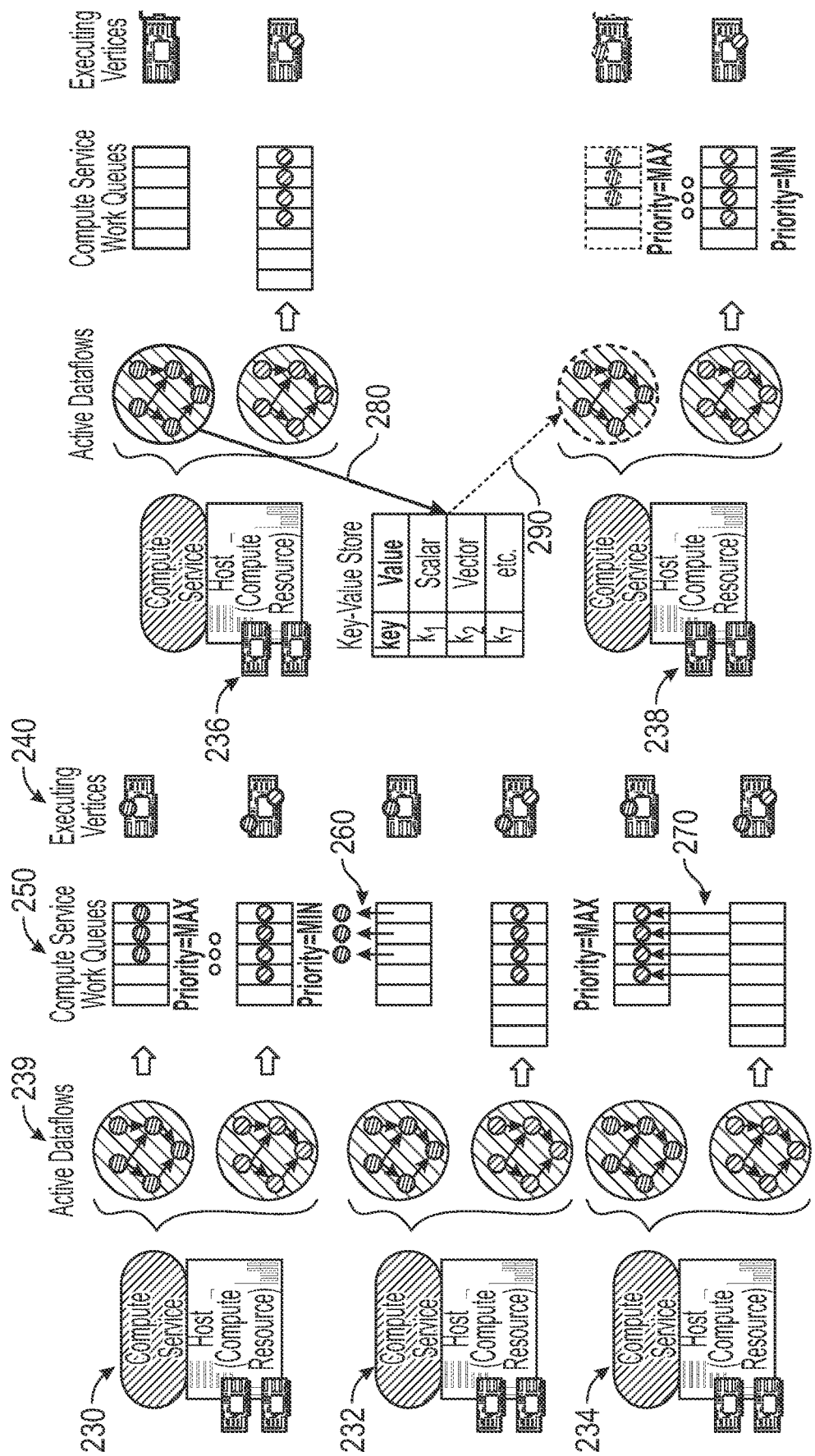
FIG. 15 shows a schematic diagram implementing changes in dataflow priority, stopping dataflow and resuming dataflow in accordance with one or more aspects of the present disclosure.

FIG. 15 is a schematic diagram illustrating pausing or stopping a dataflow computation with the ability to resume at the same point where the dataflow was paused or stopped. This is advantageous because a lengthy or processor intensive computation does not have to be restarted from the beginning. At any point, active dataflows 239 have a combination of executing 240 and queued work 250. The host 230 (compute resource) along with the compute processing service includes two active dataflows with a minimum and maximum priority queues as well as executing vertices. Clients can change dataflow priority or stop the data flow in response to external events. To accomplish this, the compute processing services remove vertices from work queues or place them on work queues of lower priority. The host (compute resource) 232 with the compute processing service is able to remove vertices from the work queue 260. Compute processing services always allow executing vertex computations to complete. Similarly and simultaneously, a different dataflow could have its priority raised. Its vertices begin to be dispatched at the new higher priority. The host 234 is an example where the vertices from a lower priority are raised to max priority in the work queue 270. Once a stopped dataflow's last vertex completes execution, the KVS contains the updated state of the computation 280 for the host 236. The KVS retains the state despite the inactive dataflow. The computation can then be restarted by using the current contents of the KVS to determine which vertices are executable and reschedule the executable vertices. This effectively resumes 290 the computation from the point at where it was paused or stopped at the host 238.

The advantages of the present disclosure described above include wide market application by allowing the same software to support low-end to high-end systems without modification, accommodating larger caseloads by adding computing resources without any changes to application software using the infrastructure and controlling system costs due to different systems configured to share hardware and software computing resources. The present disclosure is real-time capable with a low latency design and implementation, priority-preemptive scheduling of work, preempted work in progress may resume from the point of preemption. Another advantage includes minimal administration for the shared compute service. There are no requirements for software deployments, hardware upgrades, or other servicing changes. Software upgrades may be done remotely. The shared compute processing service allows for continuous and unattended operation.

Figure 16:
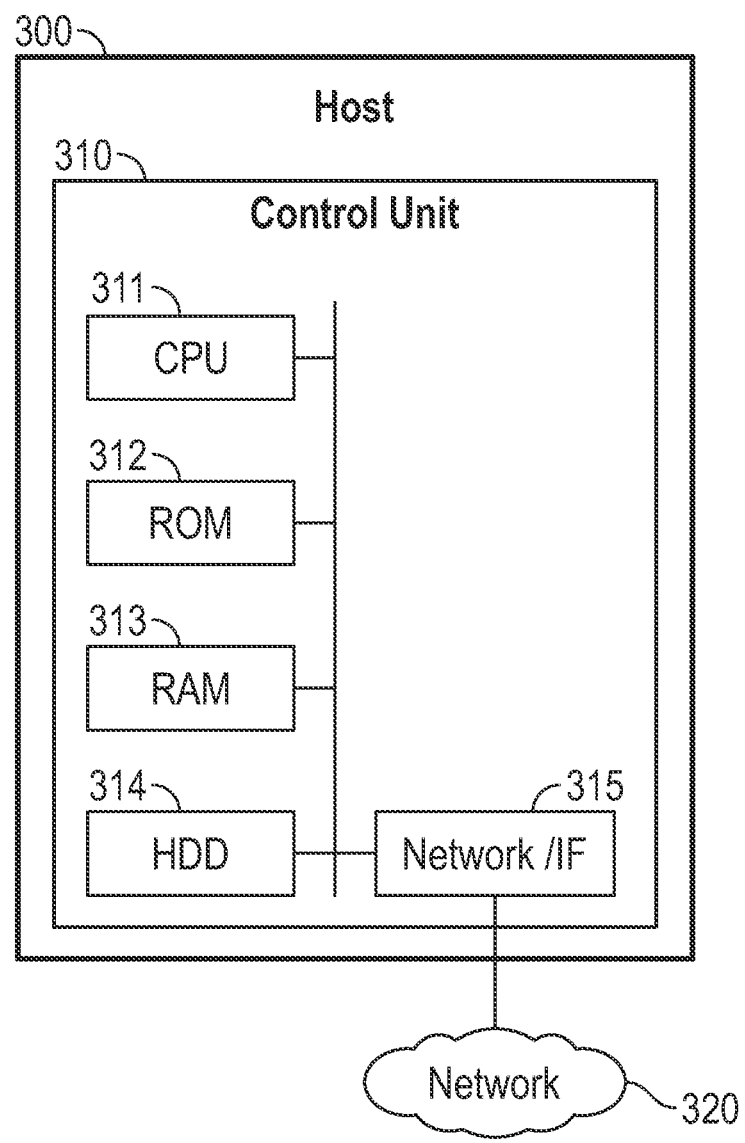
FIG. 16 illustrates an exemplary hardware configuration of a host system in accordance with one or more aspects of the present disclosure.

FIG. 16 illustrates a hardware configuration of a host device 300. Alternatively, the hardware configuration of FIG. 16 may also be used for an imaging system, a compute processing service or a third-party service in accordance with the present disclosure. The hardware configuration includes a control unit 310 including a CPU 311, a ROM 312, a RAM 313, an HDD 314, and a network I/F 315. The CPU 311 controls operations of the entire apparatus by executing various types of processing by reading out a control program stored in the ROM 312. The RAM 313 is used as a main memory of the CPU 311, and a temporary storage region, such as a work area. The HDD 314 is a large-volume storage unit that stores image data and various programs. The network I/F 315 is an interface that connects the host device to the network 320. The host receives a processing request from another apparatus via the network I/F 315, and transmit/receive various types of information.

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. A control method for controlling data processing acquired from medical imaging modalities, by using multiple data processors connected to the multiple medical imaging modalities via a computer network, the control method comprising:
   obtaining imaging information for imaging to be performed with an imaging modality of the multiple medical imaging modalities;
   obtaining, before the imaging is completed, load information of the multiple data processors;
   allocating, based on a graph information generated based on the obtained load information, at least a part of the multiple data processors to processing of data acquired in imaging based on the imaging information; and
   performing processing of the acquired data with the allocated data processing resource,
   wherein the graph information is a dataflow graph, each node of the dataflow graph specifying a processing step and each edge of the dataflow graph connecting two nodes to specify a route a processing result follows from one processing step to a next processing step, wherein data flowing at each edge of the dataflow graph is not shared among the multiple data processors and each node of the dataflow graph is a computation that can be shared among the multiple data processors.

2. The method of claim 1, wherein all nodes of the dataflow graph are executed in parallel whose edges have data that is available from prior nodes completing execution.

3. The method of claim 1, wherein each node from the dataflow graph represents the processing of data acquired in imaging based on the imaging information.

4. The method of claim 3, wherein a state of the processing of data acquired in imaging based on the imaging information is stored in a memory.

5. The method of claim 4, wherein a set of all node operands in the dataflow graph are stored in the memory.

6. The method of claim 5, wherein each medical imaging modality from the multiple medical imaging modalities corresponds to one key-value store.

7. The method of claim 1, wherein the processing of data acquired in imaging based on the imaging information corresponds to a specific medical imaging modality, the specific medical imaging modality can only access an associated key-value store.

8. The method of claim 1, wherein the imaging information is expressed within the dataflow graph.

9. The method of claim 1, further comprising:
   assigning priorities to the processing of data acquired in imaging based on the imaging information by a client application; and
   executing the processing of data in accordance with available computing resources.

10. The method of claim 1, wherein the load information is used to determine which data processor from the multiple data processors has a smallest computation cost to process data using the data processor with the smallest computation cost.

11. The method of claim 1, wherein the multiple medical imaging modalities include any combination from X-ray imaging modality, computed tomography (CT) scan imaging modality, magnetic resonance imaging (MRI) modality, ultrasound imaging modality and PET scan imaging modality.

12. The method of claim 1, wherein the multiple data processors include at least two of a central processing unit (CPU), graphics processing unit (GPU), hardware compute accelerator, field-programmable gate array (FPGA), Artificial Intelligence (AI) accelerator.

13. The method of claim 1, wherein the imaging information is obtained from a radiology information system (RIS) or a hospital information system (HIS).

14. The method of claim 1, wherein each processing step of the dataflow graph is executed in an order that is dependent upon a specification of an imaging modality used for imaging, a type of image reconstruction process to be performed, or a type of image filtering process to be performed.

15. The method of claim 14, wherein a dataflow name of the dataflow graph enables a processing server to determine the imaging modality used for imaging, the type of image reconstruction process to be performed, or the type of image filtering process to be performed.

16. The method of claim 1, wherein an imaging modality is designated as a prioritized imaging modality and processing of data associated with the imaging modality that is designated is executed prior to the processing of data associated with an imaging modality that has not been designated.

17. A processing server for controlling data processing acquired from medical imaging modalities, the processing server comprising:
   one or more memories storing instructions; and
   one or more processors executing the instructions to:
   obtain imaging information for imaging to be performed with an imaging modality from multiple medical imaging modalities;
   obtain, before the imaging is completed, load information of multiple data processors connected to the multiple medical imaging modalities;
   allocate, based on a graph information generated based on the obtained load information, at least a part of the multiple data processors to processing of data acquired in imaging based on the imaging information; and
   perform processing of the acquired data with the allocated data processing resource,
   wherein the graph information is a dataflow graph, each node of the dataflow graph specifying a processing step and each edge of the dataflow graph connecting two nodes to specify a route a processing result follows from one processing step to a next processing step, wherein data flowing at each edge of the dataflow graph is not shared among the multiple data processors and each node of the dataflow graph is a computation that can be shared among the multiple data processors.

18. A non-transitory computer-readable storage medium storing at least one program that operates to cause one or more processors to execute a control method for controlling data processing acquired from medical imaging modalities, by using multiple data processors connected to the multiple medical imaging modalities via a computer network, the control method comprising:

obtaining imaging information for imaging to be performed with an imaging modality of the multiple medical imaging modalities;

obtaining, before the imaging is completed, load information of the multiple data processors;

allocating, based on a graph information generated based on the obtained load information, at least a part of the multiple data processors to processing of data acquired in imaging based on the imaging information; and performing processing of the acquired data with the allocated data processing resource, wherein the graph information is a dataflow graph, each node of the dataflow graph specifying a processing step and each edge of the dataflow graph connecting two nodes to specify a route a processing result follows from one processing step to a next processing step, wherein data flowing at each edge of the dataflow graph is not shared among the multiple data processors and each node of the dataflow graph is a computation that can be shared among the multiple data processors.

19. A method for controlling data processing acquired from medical imaging modalities, by using multiple data processors connected to the multiple medical imaging modalities via a network, the method comprising:

receiving imaging information that is generated by the medical imaging modalities;

compiling a dataflow graph based on the received imaging information, the dataflow graph including a plurality of nodes, wherein each node from the plurality of nodes represents an imaging computation; and executing the imaging computation for each node of the dataflow graph, wherein, the execution of each node is allocated to the multiple data processors to generate an image based on the imaging information received from the multiple medical imaging modalities, wherein each edge of the dataflow graph connects two nodes and data flowing at each edge is not shared among the multiple data processors.

* * * * *